United States Patent [19]

Silvestri et al.

[11] Patent Number: 4,990,336

[45] Date of Patent: Feb. 5, 1991

[54] SUSTAINED RELEASE DOSAGE FORM

[75] Inventors: Loui J. Silvestri, Miramar; H. Ruth Pyle, Ft. Lauderdale, both of Fla.

[73] Assignee: BioSearch, Inc., Pembroke Pines, Fla.

[21] Appl. No.: 308,225

[22] Filed: Feb. 8, 1989

[51] Int. Cl.$^5$ ............... A61K 39/00; A61K 39/35; A61K 39/36; A61K 9/14

[52] U.S. Cl. .................... 424/426; 424/88; 424/89; 424/91; 424/428; 424/486; 424/496; 424/543

[58] Field of Search ............... 424/422-426, 424/428, 486, 497, 543, 88, 89, 91, 92

[56] References Cited

U.S. PATENT DOCUMENTS

| | | | |
|---|---|---|---|
| 3,329,574 | 7/1967 | Barron et al. | 424/424 |
| 3,541,201 | 11/1970 | Brown. | |
| 3,761,585 | 9/1973 | Mullan et al. | 424/91 |
| 3,773,919 | 11/1973 | Boswell et al. | |
| 3,792,159 | 2/1974 | Green et al. | 424/91 |
| 3,794,630 | 2/1974 | Mullan et al. | 260/112 R |
| 3,825,525 | 7/1974 | Mullan et al. | 260/112 R |
| 3,893,993 | 7/1975 | Mullan et al. | 260/112 R |
| 3,903,067 | 9/1975 | Mullan et al. | 260/112 R |
| 3,976,071 | 8/1976 | Sadek | 424/22 |
| 3,978,203 | 8/1976 | Wise | 424/22 |
| 4,021,364 | 5/1977 | Speiser et al. | |
| 4,070,455 | 1/1978 | Green et al. | 424/91 |
| 4,093,709 | 6/1978 | Choi et al. | 424/424 |
| 4,131,648 | 12/1978 | Choi et al. | 424/484 |
| 4,140,679 | 2/1979 | Malley | 260/857 R |
| 4,158,705 | 6/1979 | Malley | 424/91 |
| 4,164,560 | 8/1979 | Folkman et al. | 424/22 |
| 4,180,562 | 12/1979 | Patterson et al. | 424/91 |
| 4,215,036 | 7/1980 | Malley | 260/112 R |
| 4,220,565 | 9/1980 | Katz | 260/6 |
| 4,222,907 | 9/1980 | Katz | 260/6 |
| 4,226,853 | 10/1980 | Marsh | 424/91 |
| 4,234,569 | 11/1980 | Marsh | 424/91 |
| 4,253,996 | 3/1981 | Katz | 260/6 |
| 4,256,732 | 3/1981 | Malley | 424/91 |
| 4,261,973 | 4/1981 | Lee et al. | 424/78 |
| 4,269,764 | 5/1981 | Patterson et al. | 260/112 R |
| 4,276,206 | 6/1981 | Katz | 260/6 |
| 4,293,539 | 10/1981 | Ludwig et al. | 424/19 |
| 4,329,332 | 5/1982 | Couvreur et al. | 424/9 |
| 4,338,297 | 7/1982 | Michael et al. | 424/91 |
| 4,351,337 | 9/1982 | Sidman | 128/260 |
| 4,391,797 | 7/1983 | Folkman et al. | 424/19 |
| 4,428,932 | 1/1984 | Overell | 424/91 |
| 4,439,199 | 3/1984 | Amkraut et al. | 424/88 |
| 4,469,677 | 9/1984 | Michael et al. | 424/91 |
| 4,489,055 | 12/1984 | Couvreur et al. | 424/7.1 |
| 4,489,056 | 12/1984 | Himmelstein et al. | 424/22 |
| 4,526,938 | 7/1985 | Churchill et al. | 525/415 |
| 4,609,547 | 9/1986 | Garman et al. | 424/88 |
| 4,638,045 | 1/1987 | Kohn et al. | 530/323 |
| 4,675,189 | 6/1987 | Kent et al. | 424/490 |
| 4,675,381 | 6/1987 | Bichon | 530/345 |
| 4,683,288 | 7/1987 | Tanaka et al. | 528/361 |
| 4,713,244 | 12/1987 | Bawa et al. | 424/429 |
| 4,713,249 | 12/1987 | Schröder | 424/488 |
| 4,741,872 | 5/1988 | De Luca et al. | 264/47 |
| 4,757,128 | 7/1988 | Domb et al. | 528/271 |
| 4,767,628 | 8/1988 | Hutchinson | 424/426 |
| 4,774,074 | 9/1988 | Snipes | 424/19 |

OTHER PUBLICATIONS

MEDISORB TM : Bioresorbable Polymers (Properties, Uses, Storage and Handling), DuPont Company, date is belived to be Mar. 1989.

Primary Examiner—Merrell C. Cashion, Jr.
Assistant Examiner—G. S. Kishore
Attorney, Agent, or Firm—Wegner, Cantor, Mueller & Player

[57] ABSTRACT

A multiphasic sustained release injectable delivery system is provided, as well as a method for treating humans and other mammals with that multiphasic sustained release system. The multiphasic sustained release system comprises prolonged, controlled delivery of microencapsulated allergen extract comprising allergen extract encapsulated in microcapsules of bioerodible encapsulating polymer, which permits a subtained, multiphasic release of said allergen extract, including (i) a first portion of allergen extract that upon injection is capable of being released from said microcapsules of bioerodible encapsulating polymer in a manner whereby only a relatively small amount of said allergen extract is released during said first phase, whereby initial allergenicity is minimized due to said first portion producing a mild local reaction similar to that normally observed with low doses of conventional allergen administration; and (ii) secondary portions of allergen extract that provide a substantially higher level of allergen extract in doses which could provoke a serious reaction in the patient, but for the prior release of said first portion.

20 Claims, No Drawings

SUSTAINED RELEASE DOSAGE FORM

In accordance with a first aspect of the present invention there is provided a multiphasic sustained release injectable delivery system for prolonged, controlled delivery of microencapsulated allergen extract comprising allergen extract encapsulated in microcapsules of bioerodible encapsulating polymer, which permits a sustained, multiphasic release of said allergen extract, including (i) a first portion of allergen extract that upon injection is capable of being released from said microcapsules of bioerodible encapsulating polymer in a manner whereby only a relatively small amount of said allergen extract is released during said first phase, whereby initial allergenicity is minimized due to said first portion producing a mild local reaction similar to that normally observed with low doses of conventional allergen administration; and (ii) secondary portions of allergen extract that provide substantially higher levels of allergen extract in doses which could provoke a serious reaction in the patient, but for the prior release of said first portion.

In accordance with a second aspect of the present invention there is provided a method of allergen desensitization therapy for living organisms, particularly humans and other mammals which comprises injecting a subject with a microencapsulated allergen extract, a first portion of which is capable of being released in a manner whereby only a relatively small amount of said allergen extract is released during said first phase, whereby initial allergenicity is minimized due to said first portion producing a mild local reaction similar to that normally observed with low doses of conventional allergen administration; and (ii) secondary portions of allergen extract that provide substantially higher levels of allergen extract in doses which could provoke a serious reaction in the patient, but for the prior release of said first portion.

The multiphasic sustained release injectable delivery system of the invention may include one or more allergen anti-allergic agents, stabilizing agents, adjuvant agents, and/or polymer hydrolysis modifying agents. The bioerodible encapsulating polymer is preferably chosen from a group of natural and synthetic polymers consisting of a poly(lactides) and/or poly(glycolides) and/or copolymers and derivatives thereof; non-peptide polyamino acids, poly (ortho esters); low and high molecular weight polyanhydrides; polyiminocarbonates; poly alpha-aminoacids; polyalkyl-cyano-acrylate; polyphosphazenes, or acyloxymethyl polyaspartate and polyglutamate copolymers.

The allergenic extract generally comprises of one or more allergens selected from the group of pollens, molds, foods, animal danders or their excretions, smuts and insects, their venoms or their excretions. In a preferred embodiment, the allergenic extract used is in aqueous form. The allergens also may be physically or chemically modified. In a preferred embodiment, highly allergenic, low molecular weight allergen fractions have been excluded from the chemically modified allergenic extract. In a further preferred embodiment, the allergens have been lyophilized. In another embodiment, stabilizing agents are used for the allergen extract; preferred embodiments are thermopreservatives of which may be mentioned glycerine or mannitol.

In a preferred embodiment, anti-allergic agents are included which are the antihistamines diphenhydramine, chlorpheniramine, clemastine, hydroxyzine, terfenadine or promethazine, and/or the mast cell stabilizer cromolyn sodium.

In a preferred embodiment, an adjuvant is added which is tyrosine, polytyrosine, dimethylglycine (DMG), or muramyl dipeptide.

In a preferred embodiment, a polymer hydrolysis modifying agent is included which is a non-toxic organic acid or base, or an acidic, neutral or basic inorganic salt, or a solution thereof.

In a preferred embodiment, the variable release rate of allergens from the polymer is achieved heterogeneously by using a mixture of two or more of the following microsphere types:

1. Some types of microspheres have thinner allergen-impregnated polymer layers, and others which have thicker allergen impregnated polymer layers.
2. Some types of microspheres which have higher concentrations of polymer, and others which have lower concentrations of polymer.
3. Some types of microspheres which have different ratios of copolymers which affect their rate of erosion.
4. Some types of microspheres which are made of one class of polymers, and others which are made of a different class of polymer with an intrinsically different means or rate of bioerosion.
5. Some types of microspheres which have higher concentrations of impregnated allergen, and others which have lower concentrations of impregnated allergen.

In a preferred embodiment, the variable release rate of allergens from the polymer is achieved homogeneously by using just one of the following types of microspheres:

1. Some types of microspheres which have thicker allergen-impregnated outer polymer layers, and thinner allergen impregnated polymer layers in the core.
2. Some types of microspheres in which there is a higher concentration of polymer in the outer layers of the microsphere, than in the core of the microsphere.
3. Some types of microspheres which have different ratios of copolymers.
4. Some types of microspheres in which the core of each microsphere is made of one class of polymers, and in which the outer layers are made of a different class of polymer with an intrinsically different means or rate of bioerosion.
5. Some types of microspheres in which the core of each microsphere contains a higher concentration of impregnated allergen as compared to outer layers of each microsphere.

In a preferred embodiment, the variable release rate of allergens from the polymer is achieved through the use of a heterogeneous mixture of microspheres, some of which have hydrolysis accelerating agents impregnated in the microsphere polymer layers, while other microspheres contain hydrolysis retarding agents, or no accelerating/retarding agent at all.

EXAMPLE 1

A heterogeneous microcapsule composition is provided wherein the final product is an admixture of one lot of microcapsules containing a 50:50 ratio of the excipients poly(lactide-co-glycolide) copolymer, and the second lot of microcapsules containing a 70:30 ratio of the excipients poly(lactide-co-glycolide) copolymer. The allergen is an aqueous extract of short ragweed (Ambrosia artemisifolia) present at approximately 0.4%

(w/w), and no adjuvant or polymer hydrolysis-modifying agent is present. In two separate preparations, a total of 4.0 g of the excipient (in one case at a ratio of 50:50, and in the other 70:30) is dissolved in 200 g of methylene chloride. This solution is poured into a 250 ml round bottom flask fitted with a stainless steel swivel paddle and a light-duty, variable speed stirrer. A total volume of 1.5 ml of the allergen protein in buffered saline solution containing 10 mg/ml (as measured by the ninhydrin protein assay) is added to a 5 ml vial. The contents of the round bottomed flask are stirred at 3,000 rpm while the solution containing the allergen protein is slowly added. Alternatively, the mixture could be emulsified by ultrasonics or a high pressure homogenizer.

With continued stirring, 50 ml of silicone oil is added at the rate of 5.0 ml/minute using a peristaltic pump. The addition of the silicone oil results in the separation of the polymer phase and its subsequent deposit as droplets of solvent-swollen polymer onto the surface of the water-allergen microdroplets. These solvent-swollen polymer droplets are then coalesced to form a continuous film around the water-polypeptide microdroplets.

Hardening of the microcapsules is achieved by pouring the contents of the round bottom flask into approximately 1500 ml of heptane. This mixture is stirred at approximately 1000 rpm for 30 minutes using the same stainless steel stirrer. The liquid phase (containing heptane-methylene chloride-silicone oil) is removed by using a Buchner funnel loaded with Whatman #41 or #541 filter paper. The microcapsules are repeatedly washed with 100 ml aliquots of heptane to insure complete removal of the liquid phase, especially the silicone oil Finally, the microcapsules are washed with deionized water followed by a wash with a 1% (w/v) solution of Tween 20 and dried at room temperature in vacuuo. Microcapsules prepared in this fashion have diameters ranging from 5–50 microns.

EXAMPLE 2

The procedure of Example 1 is repeated, except 50 mg/ml protein of the ragweed allergen extract is used. The resulting microspheres are then resuspended in 2.0 ml of an aqueous solution of ragweed allergen at only 10 mg protein/ml. Next, a total of 4.0 g of the excipient is dissolved in 200 g of methylene chloride, and this solution is poured into a 250 ml round bottom flask as described in Example 1. While rapidly stirring this mixture, the previously-prepared microspheres (now suspended in the aqueous solution of ragweed allergen) are slowly poured into the reaction flask. Immediately, 50 ml of silicone oil is added at the rate of 5.0 ml/minute. The product is processed as described in Example 1. The resulting product consists of microspheres containing ragweed allergen at 200 mg/ml, miorospheres containing ragweed allergen 25 mg/ml, and microspheres containing ragweed allergen with a core at 200 mg/ml and a "shell" at 25 mg ragweed protein/ml. The microspheres range in size from 5 to 400 u, and are separated by mechanical sifting into various sizes. Dissolution studies demonstrate a desirable multiphasic release profile for the larger (i.e., >200 u) microspheres, thus indicating that the larger microspheres are predominantly hybrids.

EXAMPLE 3

The procedure of Example 1 is repeated, except that Timothy grass (*Phleum pratense*) allergen is substituted for short ragweed, diketene acetal-diol condensates (diketene acetal 3,9-bis-[methylene]-2,4,8,10-tetraoxaspiro [5,5]undecane condensed with 1,6-hexanediol) is substituted for the (lactide-co-glycolide) copolymer, and an adjuvant (glycodipeptide N-acetyl-muramyl-L-alpha-aminobutyryl-D-isoglutamine) is incorporated into the aqueous phase.

EXAMPLE 4

A total of 1.0 g of Poly(ortho ester) is dissolved in 25 ml methylene chloride. A total of 0.1 g of allergen protein from the house dust mite (*Dermatophagoides farinae*) is dissolved in phosphate buffered saline and 0.1% acetic acid. The microspheres are then prepared as described in Example 1.

EXAMPLE 5

Example 4 is repeated, except that the house dust mite allergen had 0.1% sodium carbonate is incorporated into the aqueous solution.

EXAMPLE 6

The microspheres prepared by Example 4 ("acid" microspheres) are mixed with microspheres from Example 5 ("basic" microspheres) in a ratio of 1:1, 1:5, and 1:10 of "acid" to "base" microspheres, respectively. By preparing various mixtures of "acid" to "base" microspheres in this manner, the release profile of the product is dramatically changed. Specifically the 1:1 mixture resulted in a slow initial release, and only a slightly elevated secondary release, whereas the 1:10 mixture resulted in an intermediate initial release, and a highly elevated secondary release.

EXAMPLE 7

The procedure of Example 1 is repeated in substantial measure, except that a glutaraldehyde-modified ragweed allergen extract is used.

EXAMPLE 8

The procedure of Example 1 is repeated except an alumadsorbed ragweed allergen extract is used.

EXAMPLE 9

The procedure of Example I is followed, except microspheres are prepared with 5–60% glycerol incorporated into the aqueous phase as a thermopreservative for the ragweed allergen extract.

EXAMPLE 10

This experiment is essentially the same as Example 1, except ragweed pollen instead of a aqueous ragweed extract is incorporated into the microspheres.

EXAMPLE 11

This experiment is essentially the same as Example 1, except lyophilized ragweed extract instead of a aqueous ragweed extract is incorporated into the microspheres.

EXAMPLE 12

This experiment is essentially the same as Example 2, except the reencapsulation is performed with an aqueous solution devoid of allergen. The final product consists of small microspheres without encapsulated allergen, small microspheres with the original concentration of allergen, and large microspheres that have an allergen core, but a thick encapsulating wall. These latter microspheres are appropriate in admixtures with thinwalled microsphere to produce the desired multi-linear release profile.

What is claimed is:

1. A multiphasic sustained release injectable delivery system for prolonged, controlled delivery of microencapsulated allergen extract comprising allergen extract encapsulated in microcapsules of bioerodible encapsulating polymer, which permits a sustained, multiphasic release of said allergen extract, including:
   (i) a first portion of allergen extract that upon injection is released from said microcapsules of bioerodible encapsulating polymer in a quantity sufficient to stimulate an immune response, but insufficient to trigger serious allergenic adverse reactions; and
   (ii) a second portion of allergen extract that is released from said microcapsules to provide a level of allergen extract in doses which could provoke a serious reaction in the patient had the first portion not been administrated;

wherein said bioerodible encapsulating polymer is selected from the group consisting of poly(lactides), poly(glycolides), non-peptide polyamino acids, poly(ortho esters), polyanhydrides, polyiminocarbonates, poly(alpha-aminoacids), polyalkyl-cyano-acrylate, polyphosphazenes, acyloxymethyl polyaspartates, polyglutamates, and copolymers and combinations thereof.

2. A multiphasic sustained release injectable delivery system for prolonged, controlled delivery of microencapsulated allergen extract in accordance with claim 1, wherein the total amount of allergen extract in said second portion is at a level higher than the toxic level for said allergen extract, in the absence of the prior release of said first portion.

3. A multiphasic sustained release injectable delivery system for prolonged, controlled delivery of microencapsulated allergen extract in accordance with claim 1 further comprising an antiallergic agent and, wherein the serious reaction caused by the released allergens is controlled by the synchronous release of said antiallergic agent.

4. A multiphasic sustained release injectable delivery system of claim 3 wherein said antiallergic agent is selected from the group consisting of diphenhydramine, chlorpheniramine, clemastine, hydroxyzine, terfenadine, promethazine and cromolyn sodium.

5. A multiphasic sustained release injectable delivery system for prolonged, controlled delivery of microencapsulated allergen extract of claim 1, wherein said allergen extract is of an allergen selected from the group consisting of a pollen, mold, food, animal dander, animal excretion, smut, insect, insect venom and insect excretions.

6. A multiphasic sustained release injectable delivery system for prolonged, controlled delivery of microencapsulated allergen extract of claim 1, wherein the multiphasic release rate is achieved by providing a heterogeneous mixture of microspheres of bioerodible encapsulating polymers, a portion of said microspheres corresponding to the first portion (i) being selected from the group consisting of:
   a. microspheres having thinner allergen-impregnated polymer layers relative to the microspheres of the second portion (ii);
   b. microspheres having higher concentrations of bioerodible polymer relative to the microspheres of the second portion (ii);
   c. microspheres having lower concentrations of impregnated allergen relative to the microspheres of the second portion (ii);
   d. microspheres composed of bioerodible polymers with an intrinsically different means or rate of bioerosion relative to the microspheres of the second portion (ii); and
   e. combinations thereof.

7. A multiphasic sustained release injectable delivery system for prolonged, controlled delivery of microencapsulated allergen extract of claim 1, wherein the multiphasic release rate is homgeneously achieved by using only one of the following types of microspheres selected from the group consisting of:
   a. microspheres which have thicker allergen-impregnated outer polymer layers relative to allergen-impregnated layers in the core;
   b. microspheres in which there is a higher concentration of polymer in the outer layers of the microsphere relative to the core of the microsphere;
   c. microspheres which have different ratios of copolymers in the outer layers relative to the core;
   d. microspheres in which the outer layers are made of a first class of bioerodible polymer, and in which the core of each microsphere is made of a second class of bioerodible polymer with an intrinsically different means or rate of bioerosion relative to said first class of bioerodible polymer; and
   e. microspheres in which the outer layers of each microsphere contains a lower concentration of impregnated allergen relative to the core of each microsphere, wherein the allergen extract of the first portion (i) is contained in the outer layers and the allergen extract of the second portion (ii) is contained in the core.

8. A multiphasic sustained release injectable delivery system for prolonged, controlled delivery of microencapsulated allergen extract of claim 1, wherein the multiphasic release rate is achieved by providing a mixture of microspheres, those corresponding to said first portion (i) including hydrolysis retarding agents impregnated in the microsphere polymer layers, while the microspheres corresponding to said second portion (ii) contain hydrolysis accelerating agents, or no accelerating agent at all.

9. A multiphasic sustained release injectable delivery system of claim 8 wherein said hydrolysis retarding and accelerating agents are each selected from the group consisting of pharmaceutically acceptable organic acids and bases, acidic, neutral and basic inorganic salts, and solutions thereof.

10. A multiphasic sustained release injectable delivery system of claim 1 wherein an allergen stabilizing agent is encapsulated along with the allergen.

11. A multiphasic sustained release injectable delivery system of claim 10 wherein said allergen stabilizing agent is a thermopreservative selected from the group consisting of glycerine and mannitol.

12. A multiphasic sustained release injectable delivery system of claim 1 wherein an adjuvant is encapsulated along with the allergen.

13. A multiphasic sustained release injectable delivery system of claim 12 wherein said adjuvant is selected from the group consisting of tyrosine, polytyrosine, dimethylglycine, and muramyl dipeptide.

14. A multiphasic sustained release injectable delivery system of claim 1 wherein the encapsulated allergen is in aqueous form.

15. A multiphasic sustained release injectable delivery system of claim 1 wherein the encapsulated allergen is in lyophilized form.

16. A multiphasic sustained release injectable delivery system of claim 1 wherein the encapsulated allergen is physically or chemically modified.

17. A method of allergen desensitization therapy which comprises injecting a subject with microencapsulated allergen extract, wherein (i) a first portion of allergen extract is released from said microcapsules in a quantity sufficient to stimulate an immune response, but insufficient to trigger serious allergenic adverse reactions; and (ii) a second portion of allergen extract is released from said microcapsules to provide a level of allergen extract in doses which could provoke a serious reaction in the patient, had the first portion not been administrated;
wherein said allergen extract is encapsulated in a bioerodible encapsulating polymer selected from the group consisting of poly(lactides), poly(glycolides), non-peptide polyamino acids, poly(ortho esters), polyanhydrides, polyiminocarbonates, poly(alpha-aminoacids), polyalkyl-cyano-acrylate, polyphosphazenes, acyloxymethyl polyaspartates, poly-glutamates, and copolymers or combinations thereof.

18. A multiphasic sustained release injectable delivery system for prolonged, controlled delivery of microencapsulated allergen extract of claim 1, wherein the multiphasic release rate is achieved by providing a mixture of microspheres, wherein those microspheres corresponding to said second portion (ii) contain hydrolysis accelerating agents, whereas those microspheres corresponding to said first portion (i) either include hydrolysis retarding agents impregnated in the microsphere polymer layers, or include no hydrolysis retarding agents.

19. A multiphasic sustained release injectable delivery system of claim 18 wherein said hydrolysis retarding and accelerating agents are each selected from the group consisting of pharmaceutically acceptable organic acids and bases, acidic, neutral and basic inorganic salts, and solutions thereof.

20. A multiphasic sustained release injectable delivery system for prolonged, controlled delivery of microencapsulated allergen extract comprising unextracted allergen source material encapsulated in microcapsules of bioerodible encapsulating polymer, which permits a sustained multiphasic release of said unextracted allergen source material, including:
  (i) a first portion of unextracted allergen source material that upon injection is released from said microcapsules of bioerodible encapsulating polymer in a quantity sufficient to stimulate an immune response, but insufficient to trigger serious allergenic adverse reactions; and
  (ii) a second portion of unextracted allergen source material that is released from said microcapsules to provide a level of unextracted allergen source material in doses which could provoke a serious reaction in the patient, had the first portion not been administrated;
  wherein said bioerodible encapsulating polymer is selected from the group consisting of poly(lactides), poly(glycolides), non-peptide polyamino acids, poly(ortho esters), polyanhydrides, polyiminocarbonates, poly(alpha-aminoacids), polyalkyl-cyano-acrylate, polyphosphazenes, acyloxymethyl polyaspartates, polyglutamates, and copolymers or combinations thereof.

* * * * *